United States Patent [19]

Bennett

[11] Patent Number: 4,844,245

[45] Date of Patent: Jul. 4, 1989

[54] BLOOD COLLECTION NEEDLE DISPOSAL SYSTEM

[75] Inventor: Michael C. Bennett, Summit, N.J.

[73] Assignee: Becton, Dickinson and Company, Franklin Lakes, N.J.

[21] Appl. No.: 298,590

[22] Filed: Jan. 17, 1989

[51] Int. Cl.⁴ ............................................. B65D 25/00
[52] U.S. Cl. ..................................... 206/366; 206/367
[58] Field of Search .............. 206/366, 365, 370, 63.5, 206/37, 380, 216, 367

[56] References Cited

U.S. PATENT DOCUMENTS

| | | | |
|---|---|---|---|
| 4,452,358 | 6/1984 | Simpson | 206/366 |
| 4,466,538 | 8/1984 | Gianni | 206/366 |
| 4,738,362 | 4/1988 | Burns et al. | 206/366 |
| 4,801,013 | 1/1989 | Bruno | 206/366 |

FOREIGN PATENT DOCUMENTS 2040268  8/1980  United Kingdom ................ 206/366

Primary Examiner—Joseph Man-Fu Moy
Attorney, Agent, or Firm—Robert P. Grindle

[57] ABSTRACT

A closure is provided comprised of a thin flexible material for use on a needle disposal container so that a contaminated blood collection needle may be removed from its holder and deposited in the container without the user touching the needle or the needle hub. The device includes dual elongated tapered openings to accommodate varying diameters of needle hubs. By having dual openings, the useful life of the cap and its associated container is doubled. The cap of the invention is configured to be utilized with a large variety of collection containers of varying sizes and shapes. A feature of the invention includes chamfered surfaces at the enlarged end of each of the dual openings to provide a sharp edge which is useful for urging a needle hub out of its holder, without physically touching the needle or hub.

14 Claims, 2 Drawing Sheets

BLOOD COLLECTION NEEDLE DISPOSAL SYSTEM

BACKGROUND AND STATEMENT OF THE INVENTION

This invention relates, generally, to receptacles or containers with one-way openings for receiving blood collection needles contaminated with the blood of patients. More particularly, this invention relates to a cap which may be used with a variety of such receptacles which accommodate the user of blood collection needles by allowing for a wrenching action for gripping the hub of the needle so that the needle may be unscrewed from the rest of the collection device and subsequently thrust through the opening of the cap to be disposed of in the associated container. With such an arrangement, users of blood collection needles do not come in contact with any of the needle surface, they are not accidentally punctured by the needles and they do not need to, for any reason, touch the needles or their hubs.

In the last several years, medical practitioners and paramedical technicians hve become increasingly aware of the danger of contamination to themselves in the handling of blood collection needles, once a blood specimen has been taken from a patient who may be suffering from some contagious disease. Recently, such dangers have been intensified by the publicity engendered by the rapid increase in the spread of the Acquired Immune Deficiency Syndrome (AIDS) Virus. For that one disease alone, it is extremely important that no blood contact be made between the medical technician or practitioner's blood, and the blood of a diseased patient.

A further problem arises later, of course, after the technician or practitioner has disposed successfully of the contaminated needle without being contaminated by the needle. That is, if such needles are simply discarded in the trash of a hospital or clinic, for example, anyone handling the garbage in the long succession of the passage of the garbage from the institution to a garbage dump may be exposed to contamination by those needles simply by someone grasping a bag containing such needles and puncturing their finger, for example. Moreover, such needles may be laid aside by a physician or technician during a difficult procedure, without thinking, and someone might lean against a table or shelf where the contaminated needle is lying and contaminate their own blood with a blood sample from the needle.

While awareness of the contamination problem has increased considerably in the last two or three years, the danger of contamination has been around for a long time and a wide assortment of devices have been provided through the years to make disposal techniques safe and fast. Some devices, for example, have been developed to receive contaminated needles through an opening in the top of a container which cannot be opened. That is, the opening is surrounded by a plurality of integral flaps which are flexible and allow receipt of a sharp object through the opening. However, no one can remove the sharp objects passing through the opening in the opposite direction. This arrangement is satisfactory, providing that the needle does not have to be removed from the rest of the collection device. However, such an arrangement does not allow removal of the contaminated needle from a holder so that the holder itself may be utilized for subsequent blood collections. It follows that manual separation is required which invites contamination. Representative of such devices are containers such as those described and claimed in U.S. Pat. Nos. 4,520,926 and 4,454,944. Both of these patents include arrangements for receiving not only single and multiple sample blood collection needles, but also syringes including the entire body of the syringe.

A further arrangement of blood collection needle receiving containers for contaminated needles is taught in U.S. Pat. No. 4,466,538. The arrangement in that patent not only provides a one-way opening for receiving contaminated needles, but also, the opening includes a tapered configuration. The point of the tapered walls of the opening is to allow a large opening at one end to receive the hub of a needle. Thus, the user may move the needle hub in the opening from the large end of the opening to a more narrow portion of the opening in order to provide a wedging action so that the user may unscrew the needle hub from the rest of the blood collection assembly. Subsequent to the unscrewing manipulation, the released needle and hub are moved back toward the larger portion of the opening so the needle and hub will pass through the opening into the container below.

Difficulties have taken place in the use of such arrangements, however, in that the needle hubs have a tendency to become "hung-up" in the narrow portion of the opening so that the user must manually unwedge and move the needle hub from the narrow portion of the opening to the wider portion so that the needle and hub will drop in. This, of course, creates the danger that the technician may become contaminated with blood on the contaminated needle during this maneuver to attempt to remove the needle hub from its wedged position in the opening.

This patent also includes the provision of the top surface of the cap having a slanted top surface so as to encourage the movement of the needle hub, once it has been unscrewed from the blood collection assembly to move downwardly toward the enlarged portion of the opening in the slanted surface of the cap of the container. Nevertheless, even with the downward slant of the opening, needle hubs become wedged readily in the narrow portion during the unscrewing or wrenching action necessary or required to unscrew the needle hub from the opening.

In U.S. Pat. No. 4,375,849 a collection cup of the kind discussed herein is designed to include a cap having a specially shaped opening for bearing engagement by the cartridge structure of a double ended needle unit to permit unthreading of the needle unit from a syringe barrel as a one-handed operation, whereupon the thus-separated needle unit is intended to fall into the collection cup without direct handling by the technician. However, such cap constructions have not prevented occasional jamming of the needle unit, as discussed above with respect to U.S. Pat. No. 4,466,538 such that it becomes necessary to dislodge the needle unit manually resulting in possible contamination or injury. Other collection cup designs have included a movable cap which can be closed when the cup is full to permit cup handling for disposal purposes without contacting the used needles. However, cap constructions of this type have been susceptible to relatively easy reopening, sometimes inadvertently, resulting in potential contamination, injury, or unauthorized reuse.

In U.S. Pat. No. 4,625,877, a cap or closure is provided for incorporation into a contaminated blood collection needle assembly with the surface thereof comprised of a thin flexible material which gives upon contact or receipt of a needle assembly through the opening disposed in the cap or closure. The arrangement includes a specific configuration of opening having tapered walls in the manner discussed above. However, incorporated with the opening are a plurality of elongated slots extending from each side of the opening which provide a flexible wrenching action for the hub of a needle assembly thrust into the opening. That is, the flexible material of the cap "gives" with such a thrusting movement and then grips the hub and provides a wrenching action allowing the technician to unscrew the hub from the rest of the blood collection assembly.

Once this unscrewing action has taken place, the wrenching action is overcome simply by a further thrusting forward of the hub through the opening because of the built-in flexibility of the edges of the opening, in accordance with this invention. The tapered opening of the invention is such, that, alternatively, the unscrewed hub of the needle assembly may simply be moved toward the enlarged end of the opening for it to fall through the opening. At any rate, the flexibility of the engaging surfaces of the opening in combination with the elongated slots placed in strategic locations along each side edge thereof provides the appropriate gripping action for the hub for obtaining the unscrewing action required to release the hub from the rest of the collection assembly while still not causing the hub to be "hung-up" and wedged into the opening as was the case with the previous arrangements with rigid edges for the opening.

Certain difficulties may arise, however, with the use of this device described above particularly as related to its flexible properties in that the flexure may result in a needle being propelled away from the opening if the operator does have proper control during the unscrewing action.

With this invention, by contrast, a cap or closure is provided for incorporation into a contaminated needle collector of the kind discussed above. The cap includes dual openings tapered in the opposite direction, with each tapered opening allowing for the desired "wrenching" action to remove a contaminated needle and its associated hub from a needle holder. As discussed above, the user inserts the hub in the enlarged portion of the opening and then moves the hub toward the smaller end until the dimension of the opening is small enough to grip the hub on both sides. Thereafter, the hub may be unscrewed from the associated holder, and the needle/hub assembly dropped through the enlarged portion of one of the openings of the collector.

One of the problems with devices of the kind discussed herein is that they are made of molded plastic parts which are developed to be used only once and then discarded. The parts, when moving relative to each other, sometimes do not work as precisely as parts manufactured for repeated use. For this reason, each of the dual tapered openings has a beveled edge adjacent the enlarged end of the opening. The beveled or chamfered edge presents a "knife-edge" so-to-speak for use in aiding the final removal of the needle hub from an associated holder.

For example, during the unscrewing procedure of the hub in one of the tapered openings, the hub may become hung up in the final unscrewing action. The knife-edge provides the user with the ability to force a wedged needle hub out of the holder and into the container without any touching.

Finally, the applicant, in working with a number of nurses and lab technicians has discovered that with the great number of needles being used daily in a large hospital, for example, it is beneficial from a cost standpoint to use fairly large capacity containers for the contaminated needle. However, again because of the single use environment, and the relative costs involved, the plastic materials around exposed edges, such as the tapered openings in the cap of the invention, wear fairly rapidly. Thus, by providing dual openings coupled with the beveled edge, much longer use of the cap is provided in combination with larger containers holding a larger quantity of discarded needles.

As purely illustrative of materials which may be used to form the cap of the invention, one may select, for example, polypropylene. Another representative thermoplastic material is acrylonitrile-butadiene-styrene terpolymer. Furthermore, a thin metallic cap may be utilized. The cap or closure of the invention, if it is made of a thermoplastic material, may be stamped, vacuum formed or injection molded. Preferably, the material will be polypropylene formed to have the major surface of the cap of a thickness of 0.062 inches. The range of thickness of the surface of the cap of the invention may be within the range of between about 0.01 and 0.10 inches. The dimension of the opening will be discussed in more detail below in the description of the drawings herein. However, it should be noted that the dimension of the opening is sized to accommodate any of the conventional needles on the market, such as those of Terumo, Sherwood and Becton, Dickinson and Company.

With the foregoing and additional objects in view, this invention will now be described in more detail, and other objects and advantages thereof will become apparent from the following description, the accompanying drawings, and the appended claims.

IN THE DRAWINGS

FIG. 1 is a top plan view of a container closure for use in a sharps collection container assembly, and illustrating the configuration of opening of the invention herein; and FIG. 2 is a sectional view taken along lines 2—2 of FIG. 1.

DETAILED DESCRIPTION OF THE DRAWINGS

Figure 1:
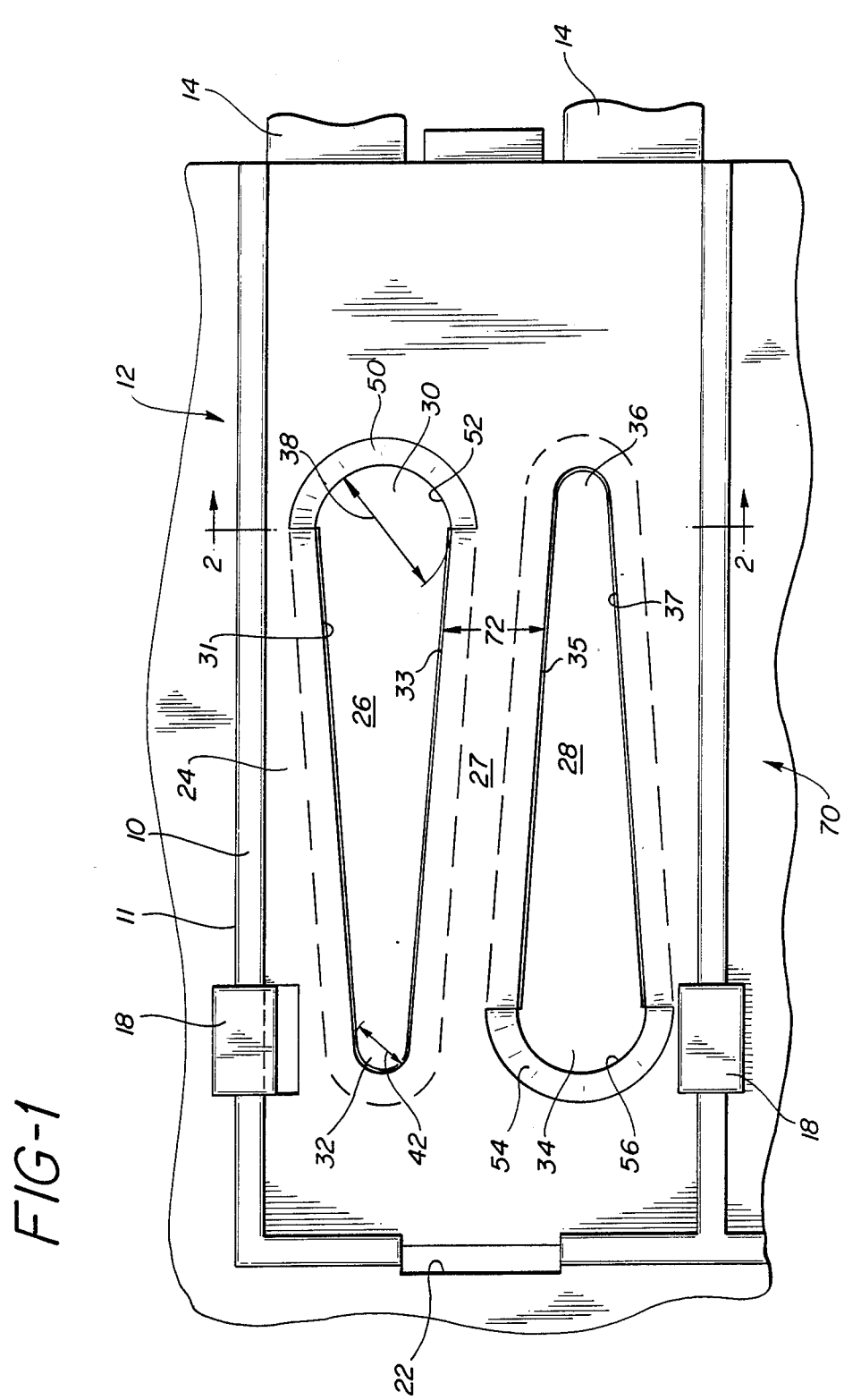

Referring to the drawings in which like reference characters refer to like parts throughout the several views thereof, an embodiment of the apparatus incorporating the invention herein is illustrated in the form of a cap for closing the opening in a blood collection needle disposal system including a container therefore. It will be understood by practitioners-in-the-art, that the cap illustrated in FIG. 1 may be utilized and incorporated into a collection container assembly wherein the container may be of a variety of configurations includuing rectangular, square or round in shape and of a variety of sizes depending upon the specific application of the collection assembly in a particular location in a hospital or clinic, for example. Also, the top surface 12, in addition to accommodating cap 10 of the invention, may include a second inserted cap 70 incorporating an enlarged opening for receiving large contaminated items such as needle holders or syringes which are in a condition to be disposed or rather than used again.

Thus, insert 10 having a border 11 may be molded into the top surface 12 of the container, as shown in FIG. 1. Insert 10, in turn, includes a molded in panel 24 which includes the formed openings of the invention. These openings 26, 28 may be positioned as shown with each end of the dual openings 26, 28 being positioned directly opposite to each other. Alternatively, the openings 26, 28 may be positioned off-set from each other in order to reduce the width of the spacer bar 27 positioned therebetween in view of space limitations which may be present with the dimensions of certain container tops.

As can be seen in FIG. 1, each opening 26, 28 includes an enlarged end and a smaller end. Thus, opening 26 includes a semi-circular enlarged end 30 and a semi-circular smaller end 32. By the same token, opening 28 includes a semi-circular smaller end 36 and a semi-circular enlarged end 34. Between the smaller semi-circle at one end and the larger semi-circle at the opposite end of each opening 26, 28 are straight line edges which form a tapered opening. Because of this, the dimensions between the opposed side edges 31, 33 of opening 26 and 35, 37 of opening 28 gradually increase or decrease as the case may be for providing the taper. These opposed surfaces provide a wedging action for a variety of different sizes of needle hubs.

Thus, the user may, for example, insert a needle hub into the enlarged end 30 of opening 26 and then gradually move the hub to the left as shown in FIG. 1 until the opposed side edges surfaces 31, 33 are small enough to grip the hub. Once the inserted hub has been gripped by the opposed edges 31, 33, the user may rotate the needle holder in the counterclockwise direction in order to unscrew the needle hub from the holder. Once it is unscrewed, the user may move the holder and the unscrewed hub to the right until the hub drops off the holder and into the container below.

As a further feature of the invention, each opening includes a chamfered or beveled edge surface 50 for opening 26 and 54 for opening 28. The chamfered surface 50, for example, provides a "knife-like" edge 52 around the front edge of the enlarged end 30 of opening 26, for example. In the event that the needle hub will not drop freely from the holder once the unscrewing action has taken place, as described above, the user may move the holder with its still depending unscrewed needle hub to the edge 52 to pry the needle hub away from the holder against the knife-like edge 52. Of course, the same procedure can take place in the reverse movement to the left for use of opening 28, its chamfered or beveled edge 54 and its front knife edge 56.

As can be seen in FIG. 1, insert 10 may include integral straps 14, only a portion of which is shown which straps connect to a cap which may be moved over the top of the openings 26, 28 for a permanent locking under locking indents 18 as shown in FIG. 1 once the container is filled with contaminated needles and/or holders. The locking detents are such that the associated cap, once placed in a locking position cannot be removed. To this end, the cap may include a locking tab which is inserted into slot 22 for this purpose.

Figure 2:
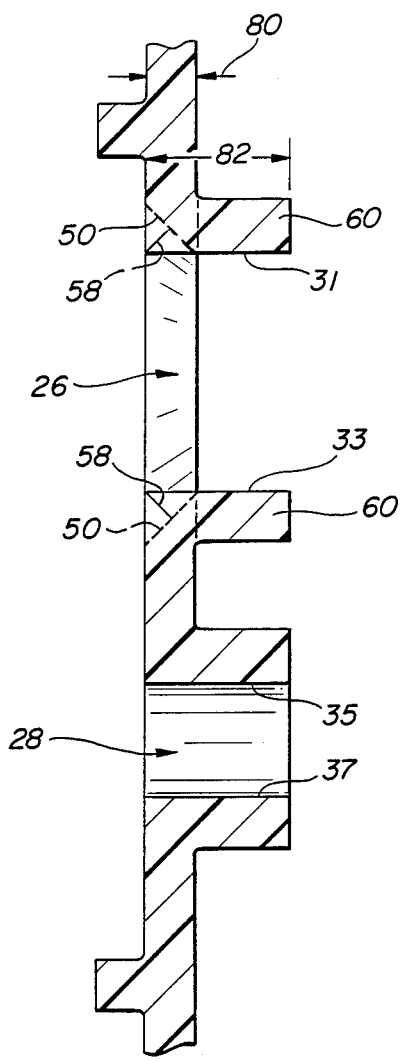

As can be seen in FIG. 2, openings 26, 28 include flanges entirely around the opening surfaces thereof indicated in FIG. 2 as 60. These flanges give the edges of openings 26, 28 a degree of strength and stability so that during the manipulation of the needle hubs for unscrewing and removal, the integrity of the side walls of the openings are maintained so that they do not deteriorate until such time as the associated containers are filled. It will be understood that the user wishes to remove the needles as quickly and as efficiently as possible and therefore cannot, under the circumstances of taking blood samples, for example, have to attempt to manipulate such devices as contaminated needles in openings which fail to hold the needle hubs appropriately for the unscrewing action.

While it will be understood by practitioners-in-the-art that a cap insert 10 will have a varying dimension depending upon the specific container into which it will be incorporated and the use for which the container will be made (i.e., heavy-duty use or light-duty use in various locations in a clinic or a hospital) as purely illustrative of dimensions of the embodiment of cap illustrating the invention herein, one may note that the diameter 38 of the enlarged semi-circular ends 30 and 34 will be within the range of between about 0.275 and 0.40 inches, and preferably 0.325 inches. By the same token, the diameter 42 of the semi-circular small ends 32, 36 of openings 26, 28, respectively, will be within the range of between about 0.1 and 0.175 inches and preferably 0.135 inches.

Referring to FIG. 2, the angle 58 of the chamfer of surfaces 50 and 54 will be, preferably, 45 degrees from the top surface of the insert 10. However, this angle may be varied within the range of between about 35 and 55 degrees.

Further as purely illustrative of the invention here, the dimension 80 shown in FIG. 2 may be, for example, 0.062 inches while the dimension 82 may be 0.188 inches. The width of the divider panel 27 between the openings 26, 28 may be 0.24 inches.

It should be understood, however, that all of these dimensions are representative only of a specific embodiment of the invention as discussed herein. The dimensions will vary, as will be understood by practitioners-in-the-art depending on the specific application of the container devices discussed above. It should be emphasized here that these dimensions are representative only to illustrate the relationship of dimensions among the various parts of the cap or closure of the invention in order to provide the proper working action of the cap. Simultaneously, the gripping and wrenching action necessary for unscrewing a needle hub is provided while the same time there is the additional knife-edge to pry the released hub to become unwedged so as to be discarded through the opening without any manual handling to remove the released hub from the opening to allow it to fall into the container. This is the specific reason for the knife-edge 52, 56 of the openings 26, 28 respectively in order to enhance the removal.

Thus, and as will be apparent from the foregoing, there are provided in accordance herewith, methods and apparatus for the release of a contaminated needle hub from the rest of a blood collection assembly and the proper gripping action therefore. Simultaneously, the required properties including a knife-edge are provided which enhance the releasing of the wrenched hub of such a contaminated needle so that it will fall easily and safely into the container therefore. Thus, the contaminated needle is removed from any contact with the technician making a contaminated blood collection and from any contact with anyone handling the disposal of goods from a hospital or clinic in the sequence of handling necessary for such removal to a garbage disposal dump or other facility provided for this purpose.

Obviously, it will be apparent that the arrangement of an invention here is of a simple configuration so that the cap of the invention may be vacuum formed or injection molded utilizing assembly line techniques so that many thousands of such caps can be produced on a mass production basis inexpensively.

While the methods and apparatus herein disclosed form preferred embodiments of this invention, this invention is not limited to those specific methods and apparatus, and changes can be made therein without departing from the scope of the invention which is defined in the appended claims.

What is claimed is:

1. A closure device for closing the opening in a contaminated needle collection container and removing contaminated needle hubs from blood collection assemblies, characterized by
   (a) a substantially flat thin closure body;
   (b) attaching means along the edges of said body for the attachment to a containment needle collection container;
   (c) a pair of openings positioned substantially centrally of said body;
   (d) each said opening being elongated with a first end and a second end;
   (e) each said first end being of smaller width than each said second end;
   (f) the side walls of each of said elongated openings diverging from its respective said first end to its respective said second end; and
   (g) each said second end having a chamfered edge forming a knife-edge for prying needle hubs stuck in needle holders.

2. The closure of claim 1, further characterized by
   (a) said body is rectangular.

3. The closure of claim 1, further characterized by
   (a) said body has a thickness within the range of between about 0.01 inches and 0.10 inches.

4. The closure of claim 1, further characterized by
   (a) said body is comprised of a material selected from the group consisting of polypropylene, acrylonitrile-butadiene-styrene terpolymer, and metal.

5. The closure of claim 1, further characterized by
   (a) said body is comprised of polypropylene having a thickness of about 0.62 inches.

6. The closure of claim 1, further characterized by a cap for permanently closing said opening comprising
   (a) a cap body;
   (b) means connecting said cap body to said closure body; and
   (c) cooperating locking means on said closure body and said cap body for permanently closing said opening in said closure body with said cap body.

7. The closure of claim 1, further characterized by
   (a) said dual openings are arranged in opposed relation to each other in said closure body so that said first end of one of said dual openings is opposite said second end of the other of said dual openings, and visa versa.

8. The closure of claim 1, further characterized by
   (a) each said second end is semi-circular with a diameter within the range of between about 0.275 and 0.40 inches.

9. The closure of claim 8, further characterized by
   (a) each said semi-circular diameter has a diameter of 0.325 inches.

10. The closure of claim 1, further characterized by
    (a) each said first end is semi-circular with a diameter within the range of between about 0.1 and 0.175 inches.

11. The closure of claim 10, further characterized by
    (a) each said first end has a diameter of about 0.135 inches.

12. The closure of claim 1, further characterized by
    (a) each said chamfered edge along said second end is formed in the top surface of said closure body at an angle thereto.

13. The closure of claim 12, further characterized by
    (a) the surface of each said chamfered edge is formed at an angle to the top surface of said closure body;
    (b) said angle being within the range of between about 35 degrees and 55 degrees.

14. The closure of claim 13, further characterized by
    (a) said angle is 45 degrees.

* * * * *